United States Patent [19]

Brandt et al.

[11] 4,349,416
[45] Sep. 14, 1982

[54] PROCESS AND DEVICE FOR THE SEPARATION OF MIXTURES WHICH FORM AN AZEOTROPE

[75] Inventors: Hans-Walter Brandt, Odenthal, Fed. Rep. of Germany; Heinrich Steude, Pittsburgh, Pa.; Ludwig Bruns; Hans-Dieter Köhler, both of Dormagen, Fed. Rep. of Germany

[73] Assignees: Bayer Aktiengesellschaft, Leverkusen; EC Erdölchemie GmbH, Cologne-Worringen, both of Fed. Rep. of Germany

[21] Appl. No.: 307,252

[22] Filed: Sep. 30, 1981

[30] Foreign Application Priority Data

Oct. 11, 1980 [DE] Fed. Rep. of Germany ....... 3038497

[51] Int. Cl.³ .......................... B01D 3/40; C07C 29/80
[52] U.S. Cl. ........................................ 203/19; 203/21; 203/23; 203/25; 203/64; 203/78; 203/84; 203/98; 203/DIG. 13; 203/DIG. 19; 202/154
[58] Field of Search ....................... 203/19, 21, 23, 25, 203/27, 64, 73, 78, 84, 98, 99, 100, DIG. 19, DIG. 13; 426/494, 493; 568/916; 196/134; 202/154

[56] References Cited

U.S. PATENT DOCUMENTS

| | | | |
|---|---|---|---|
| 1,469,447 | 10/1923 | Schneible | 203/19 |
| 1,907,834 | 5/1933 | Kyrides | 203/19 |
| 2,593,931 | 4/1952 | Stearns | 203/25 |
| 3,464,896 | 9/1969 | Washall | 203/64 |
| 4,128,457 | 12/1978 | Barba et al. | 203/DIG. 19 |
| 4,134,797 | 1/1979 | Ozero | 203/DIG. 19 |
| 4,217,178 | 8/1980 | Katzen et al. | 203/DIG. 13 |
| 4,256,541 | 3/1981 | Muller et al. | 203/DIG. 13 |
| 4,280,880 | 7/1981 | Vora et al. | 203/DIG. 19 |
| 4,292,140 | 9/1981 | Kawasaki et al. | 203/23 |
| 4,306,942 | 12/1981 | Brush et al. | 203/DIG. 19 |

*Primary Examiner*—Wilbur L. Bascomb, Jr.
*Attorney, Agent, or Firm*—Sprung, Horn, Kramer & Woods

[57] ABSTRACT

A process and apparatus for the separation of components from a mixture which forms an azeotrope is disclosed by subjecting the mixture to extractive distillation to remove one of the components and regeneration to separate another component from the extracting agent added to the extractive distillation column. According to the invention, a first side stream is withdrawn from the extractive distillation column, passed in heat exchange with the bottoms from the extractive distillation column en route to the regeneration column and returned to the extractive distillation column at a point below the point at which it is withdrawn. A second side stream from the extractive distillation column is withdrawn, passed in heat exchange with the bottoms of the regeneration zone and returned to the extractive distillation column. For this purpose, separate heat exchangers are used for the respective side streams.

14 Claims, 1 Drawing Figure

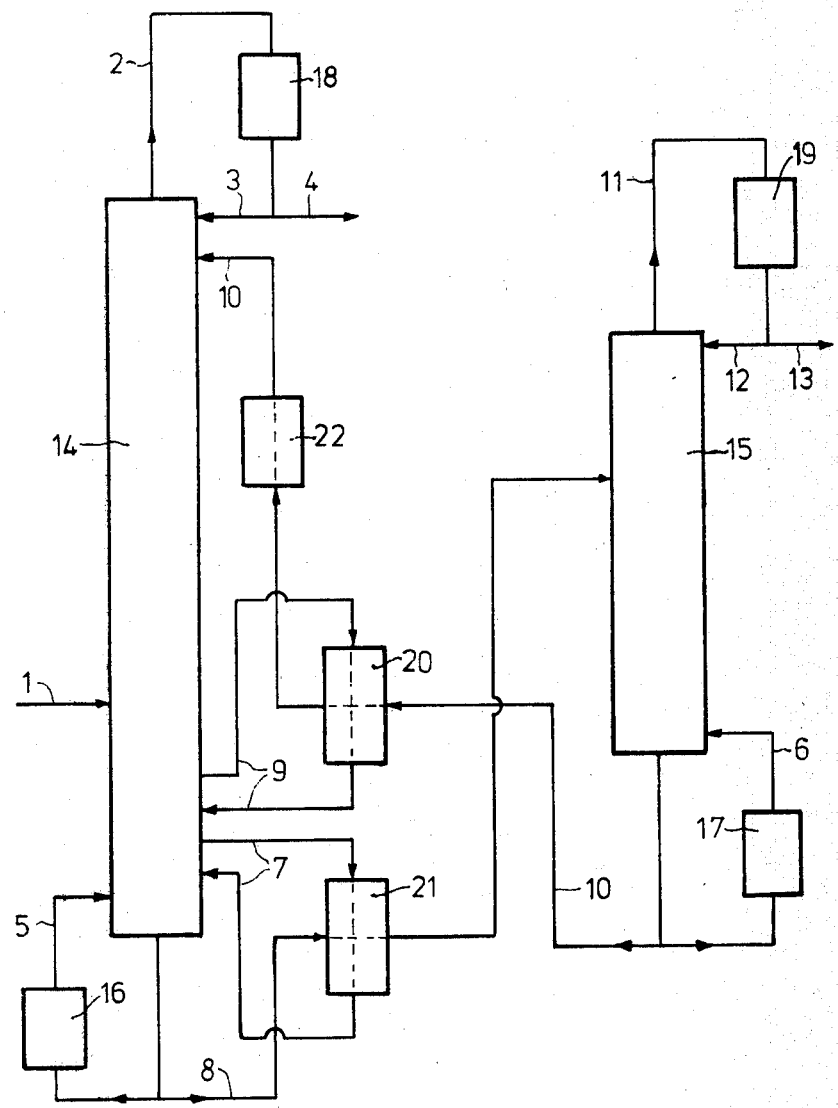

PROCESS AND DEVICE FOR THE SEPARATION OF MIXTURES WHICH FORM AN AZEOTROPE

The present invention relates to a process and a device for the separation, by means of extractive distillation, of mixtures which form an azeotrope.

There are a large number of mixtures of substances which form constant-boiling azeotropes, and which therefore cannot be separated into the pure components by simple distillation. To these mixtures belong many which are also of great importance for industrial use, such as methyl acetate/methanol, vinyl acetate/methanol, acetone/methanol, ethanol/water, allylalcohol/water and tertiary butanol/water. The most well known of these mixtures which form an azeotrope is the system ethanol/water. Many uses of the substances contained in such mixtures require a separation of the accompanying substances, the requirement for the purity to be achieved frequently being very rigorous. Using ethanol as an example, its desirable admixture to propellant gasoline—ethanol has an octane number of 120 and acts as an antiknock agent—is dependent on its residual water content being so low that no water-containing separate phase separates out from the ethanol/gasoline mixture.

The separation of the undesired accompanying substances from an azeotrope by means of chemical or physical bonding to an auxiliary substance is known. Thus, absolute (water-free) ethanol can be obtained from the ethanol/water azeotrope by treatment with dehydrating agents. Quicklime or a mixture of anhydrous sodium and calcium acetate (Ullmanns Enzyklopädie der technischen Chemie (Ullmann's Encyclopaedia of Industrial Chemistry), 4th edition, Volume 2, page 118, Verlag Chemie 1972), as well as elementary sodium, magnesium or calcium (Bull. Soc. Chim. France 1966, 2541), for example, are known as such dehydrating agents.

Furthermore, the separation of binary azeotropes, with the addition of an entrainer, is known. In this process, the undesired accompanying substance (the water in the case of the binary azeotrope ethanol/water) is removed, in general, as a ternary azeotrope which consists of the entrainer, the undesired accompanying substance to be removed and a small proportion of the principal component which is to be purified. The following compounds, for example, have become known as entrainers for the separation of the binary azeotrope ethanol/water: benzene, benzine/benzene mixture and trichloroethylene (Ullmanns Enzyklopädie der technischen Chemie (Ullmann's Encyclopaedia of Industrial Chemistry), 4th edition, Volume 2, page 117, Verlag Chemie 1972) and furthermore pentane, diethyl ether, carbon tetrachloride, ethyl chloride, ethyl acetate and butyl alcohol (U.S. Pat. No. 3,575,818).

Furthermore, the preparation of absolute ethanol from aqueous ethanol by means of extractive distillation using ethylene glycol is known (Advances in Chemistry Series No. 115 of the American Chemical Society of 24.11.1976).

There are disadvantages attached to all the processes described. Thus, the removal of water using dehydrating agents can only be carried out batchwise, and the dehydrating agent is either lost (as when metallic sodium, calcium or magnesium is used) or must be freed from water in a laborious manner for re-use (as in the case of the mixture of potassium and sodium acetate). In the case of the azeotropic distillation with the addition of an entrainer, this entrainer occurs again in traces in the desired pure principal component. This fact excludes, for example, the use in the foodstuffs or medical sector of absolute ethanol prepared in this manner, since the entrainers used industrially, such as, for example, benzene, are toxic. Furthermore, a complicated separation process is necessary, since a ternary azeotrope must first be distilled off to remove the undesired accompanying substance, only then to be able to separate the excess entrainer from the desired principal component. The energy requirement of a separation using entrainers is thereby very high. Furthermore, the distillation using an entrainer is more costly, the greater the quantity of the undesired accompanying substance present in the mixture to be separated. Therefore, firstly a concentration column is required for the binary mixture to be separated, which column is operated with a high consumption of energy and before using the entrainer, it being necessary to approach the azeotropic point closely. Furthermore, according to Ullmann (loc. cit.), a consumption of 0.5 to 0.7 kg of benzine/benzene mixture per 100 l of dewatered ethanol is to be expected. Finally, the abovementioned extractive distillation of aqueous ethanol is more expensive than the azeotropic distillation using an entrainer, as is shown in Advances in Chemistry Series No. 115, which has been mentioned, by comparison with the azeotropic distillation using n-pentane.

A process has now been found for the separation of mixtures which form an azeotrope, by means of extractive distillation using an extractive distillation column and a regeneration column for the extracting agent, which is characterised in that two side-streams of the medium in the extractive distillation column are taken off from the extractive distillation column, between the bottom and the feed point for the mixture to be separated, and one of these side-streams is allowed to participate in a heat exchange process with the bottom run-off of the extractive distillation column and the other side-stream is allowed to participate in a heat exchange process with the bottom run-off of the regeneration column, in two separate heat exchangers, and the side-streams which have been taken off are returned after the heat exchange process to the extractive distillation column, below their take-off point.

The process according to the invention is carried out in an extractive distillation column and a regeneration column. In this process, the mixture to be separated, which forms an azeotrope, is fed into the lower part of the extractive distillation column, whilst the extracting agent is fed into the upper part of this column. Having been freed of the undesired accompanying substance, the substance of the mixture to be separated is then taken off in the form of a vapour at the top of the extractive distillation column, whilst the extracting agent, which is charged with the accompanying substance, is taken off as a bottom run-off of the extractive distillation column and is introduced into the regeneration column. In the regeneration column, the undesired accompanying substance is withdrawn as the top product, whilst the purified extracting agent is taken off at the bottom of the regeneration column and can again be fed into the upper part of the extractive distillation column.

The abovementioned substances may be mentioned as examples of mixtures which form an azeotrope and are to be separated according to the invention. In general, the undesired accompanying substances here are those which are mentioned in second place, for example the methanol or the water. The ethanol/water mixture may be preferably mentioned amongst these mixtures, the process according to the invention being carried out for the preparation of absolute ethanol.

This mixture to be separated is taken off, in general, from a pre-concentration column. This pre-concentration can be carried out in such a manner that the constant-boiling azeotrope, which is formed by the mixture to be separated, is taken off. The pre-concentration can, however, also be operated in such a manner that the undesired accompanying substance is present in a higher concentration than that corresponding to the azeotrope. 0.1 to 30% by weight, preferably 1 to 20, and particularly preferably 5 to 10% by weight, in addition to the proportion in the azeotrope, may be mentioned as an example of such a higher concentration. For the ethanol/water mixture preferably to be employed, the crude ethanol with about 70 to 95.5, preferably about 75 to 95, particularly preferably about 85 to 90% by weight of ethanol can be taken off, for example, from the pre-concentration column. This latter variant, in which the undesired accompanying substance is present in higher concentration than in the azeotrope, is preferred, since the pre-concentration column can be particularly favourably operated in terms of energy in this case.

The following compounds, for example, can be employed as the extracting agent: ethylene glycol, di-, tri- or tetraethylene glycol, monoalkyl ethers thereof, for example ethylene glycol methyl ether, mixtures of the compounds mentioned, as well as N-methylpyrrolidone, dimethylacetamide, dimethylformamide or concentrated $CaCl_2$ solution.

The choice of the extracting agent can be optimally suited to the mixture to be separated in each case by simple preliminary experiments. For the ethanol/water mixture preferably to be separated according to the invention, ethylene glycol, diethylene glycol or ethylene glycol methyl ether may be preferably mentioned as examples of the extracting agent, and ethylene glycol may be particularly preferably mentioned as an example of the extracting agent. 100 to 500, preferably 150 to 350% by weight, relative to the quantity of the mixture to be separated which has been fed in, may be designated, by way of example, as the quantity of extracting agent for the ethanol/water mixture to be separated.

A column with 40 to 200, preferably 60 to 150, particularly preferably 80 to 120 trays, may be mentioned as an example of an extractive distillation column. It is operated, for example, at a pressure of 0.5 to 3 bars, preferably at atmospheric pressure. The reflux ratio is adjusted to a value of 0.5 to 2, being defined as the ratio of reflux to take-off (R/T).

A column with 12 to 50, preferably 15 to 30, trays may be mentioned as an example of a regeneration column. Since the extracting agent has a higher boiling point than the components of the mixture which is to be separated and which forms an azeotropic mixture, the regeneration column is operated, in general, at a pressure below atmospheric pressure, in order to keep the thermal load of the extracting agent at a low level. A pressure of from 30 to 900, preferably 50 to 600 mbars, may be mentioned as an example. The reflux ratio, R/T, is adjusted in the regeneration column to a value of from 0.1 to 2.0, preferably 0.5 to 1.5. The stated parameters for the regeneration column can be adjusted within the scope of the ranges mentioned in such a manner that the extracting agent is freed of all substances except for a permissible residual content of the undesired accompanying substance from the mixture to be separated. The permissible residual content of the undesired accompanying substance from the mixture to be separated is simultaneously a measure of the purity of the desired substance from the mixture which is fed in, which desired substance is obtained as the top product in the extractive distillation column. A content of from 1 to 1,000 ppm, preferably 2 to 500 ppm, particularly preferably 5 to 200 ppm, may be mentioned as an example of the residual content of undesired accompanying substance in the regenerated extraction solvent.

If there are 3 to 8, preferably 4 to 6, trays in the extractive distillation column between the feed of the regenerated extraction solvent and the feed of the reflux, it is possible to obtain a top product with less than 1 ppm of residual extraction solvent.

According to the invention, two side-streams of the medium present in the column are taken off from the extractive distillation column below the feed of the mixture which is to be separated and which forms an azeotrope. These take-off points can be from about 5 to 25 trays below the feed point for the mixture to be separated, the lower part of the stated range being appropriate for columns with a relatively small total number of trays, and the upper part of the stated range being appropriate for columns with a relatively large total number of trays. For a column with a total number of trays of 80 to 120, for example, the take-off points are about 10 to 25 trays below the feed point for the mixture to be separated. The two take-off points can be arranged at the height of the same tray, or can be undertaken at different trays. Take-off at different trays is preferred. For example, the two take-off points are 1 to 10, preferably 3 to 8 trays apart.

The two side-streams of the medium in the extractive distillation column, which side-streams have been taken off, are brought to heat exchange, in two separate heat exchangers, with the bottom run-off of the extractive distillation column or the bottom run-off of the regeneration column. In the case in which the two take-off points are arranged at different trays, the side-stream taken off further above as well as the side-stream taken off further below can be used for the heat exchange with the bottom run-off of the extractive distillation column, the other side-stream, in each case, being brought to heat exchange with the bottom run-off of the regeneration column. Preferably, the side-stream taken off further above is brought to heat exchange with the bottom run-off of the regeneration column and the side-stream taken off further below is brought to heat exchange with the bottom run-off of the extractive distillation column.

In the process according to the invention, the substances of value which are contained in the mixture fed in and are freed from the undesired component of the azeotrope, the substance being, for example, the ethanol from an ethanol/water mixture, are obtained as highly pure, water-clear distillates having less than 1 ppm of extraction solvent. This distillate of the substance of value contains less than 1,000 ppm of the undesired component; for example, the ethanol from an ethanol/water mixture contains less than 500 ppm, preferably less than 200 ppm, of water when ethylene glycol is used as the extraction solvent.

The process according to the invention is distinguished by a considerable saving of energy. Thus, for example, in the preparation of absolute ethanol from ethanol/water mixtures, less than half the expenditure of energy is needed that is required for an extractive distillation according to the abovementioned Advances in Chemistry Series No. 115. For a comparative outlay in apparatus, the process according to the invention is energetically as favourable as the azeotropic process, also mentioned in Advances in Chemistry Series No. 115, for the separation of ethanol and water with the aid of n-pentane as the entrainer, if only the pure substances obtained in the extractive distillation column or in the azeotropic distillation column are considered. However, the azeotropic distillation has a grave disadvantage compared to the extractive distillation: the desired pure component, for example the ethanol in the separation of ethanol/water mixture, appears as the bottom product in the azeotropic distillation, whilst in the extractive distillation it is produced as the top product and thereby as a distillate. For an unobjectionable comparison of the azeotropic distillation with the extractive distillation, the bottom product produced in the azeotropic distillation must consequently be distilled once more, so that the desired product is also produced as the top product and thereby as a distillate, and the expenditure in energy required for this purpose must be taken into account in the comparison. In the case of ethanol, for example, this expenditure is 200 kcal/kg of absolute ethanol. Taking this precision distillation into account, the process according to the invention is still more favourable in expenditure of energy by about 25 to 30% than the azeotropic distillation with the aid of an entrainer. This may be presented comparatively for the example of the separation of ethanol and water on the basis of values known from the literature and the values determined in the process according to the invention:

| Energy requirement for the preparation of absolute ethanol | | |
|---|---|---|
| Distillation | Literature | kcal/kg of ethanol |
| Extractive (ethylene glycol) | Adv. Chem. Series No. 115 | 1106 |
| Azeotropic (n-pentane) | Adv. Chem. Series No. 115 | 429 (without ethanol distillation) |
| Azeotropic (n-pentane) | Adv. Chem. Series No. 115 | 629 (with ethanol distillation) |
| Azeotropic (benzene) | Robinson, Gilliand, Elements for Fractional Distillation | 816 (without ethanol distillation) |
| Azeotropic (benzene) | Robinson, Gilliand, Elements for Fractional Distillation | 1016 (with ethanol distillation) |
| Extractive (ethylene glycol) | According to the invention | 450–470 |

In the process according to the invention, solvent consumptions of 0.01 kg of extraction solvent per ton of distillate taken off from the extractive distillation column, and less, are achieved, for example less than 0.01 kg of ethylene glycol per ton of absolute ethanol.

It is surprising that in spite of the take-off of two side-streams, which is to be carried out according to the invention, and the temperature discontinuity in the column arising as a consequence of the return of these side-streams after the heat exchange process, a stationary equilibrium and a trouble-free operation of the distillation can be attained.

The invention furthermore relates to a device for the extractive distillation of mixtures which form an azeotrope, consisting of an extractive distillation column and a regeneration column for the extracting agent, which is characterised by two take-off points in the extractive distillation column, between the bottom and the feed point for the mixture to be separated, for taking off a medium in the extractive distillation column, two heat exchangers, one heat exchanger being connected for heat exchange between the medium of the extractive distillation column, taken off at one take-off point, and the bottom run-off of the extractive distillation column, and the other heat exchanger being connected for heat exchange between the medium of the extractive distillation column, taken off at the other take-off point, and the bottom run-off of the regeneration column, and two recycling points, below each of the take-off points, for recycling, after the heat exchange process, of the medium taken off from the extractive distillation column.

BRIEF DESCRIPTION OF DRAWING

The annexed drawing is a flow diagram showing an apparatus for carrying out the process.

DESCRIPTION OF SPECIFIC EMBODIMENT

Referring to the drawing, the device according to the invention is to be illustrated in more detail with reference to the appended FIGURE, by way of example, wherein the case is shown in which the two take-off points are placed at different trays of the extractive distillation column, and wherein the medium taken off at the upper take-off point participates in heat exchange with the bottom run-off of the regeneration column and the medium taken off at the lower take-off point participates in heat exchange with the bottom run-off of the extractive distillation column.

The embodiment represented in the FIGURE comprises regeneration column and the medium taken off at the lower take-off point participates in heat exchange with the bottom run-off of the extractive distillation column.

The embodiment represented in the FIGURE consists of the extractive distillation column 14 and the regeneration column 15. Each of the two columns has a heating device in the bottom circulation 16 and 17. The vapours taken off at the top of the columns are condensed in each case in a condenser 18 or 19. In the heat exchanger 20 according to the invention, the stream of the column medium from 14, which is taken off at the upper take-off point, is brought into heat exchange with the bottom run-off from 15. In the heat exchanger 21 according to the invention, the stream of the medium from 14, which is taken off at the lower take-off point, is brought into heat exchange with the bottom run-off from 14. 22 is an additional heat exchanger in which, if required, the temperature of entry of the bottom run-off from 15 into 14 can be corrected by an additional cooling medium, if this is not sufficiently effected by the measure according to the invention in heat exchanger 20. The FIGURE displays the following product streams: the crude mixture 1 which forms an azeotrope and which originates from a suitable pre-concentration column (for example crude aqueous ethanol); vapours of the desired purified substance of value 2 (for example absolute ethanol); reflux 3 and take-off 4 of the condensed purified substance of value; circulation of the bottom heater 5 for 14 and 6 for 15; lower take-off with recycling 7 of the medium from 14, which participates according to the invention, in 21, in heat exchange with the bottom run-off 8 from 14, 8 being then fed into 15 for regeneration; upper take-off and recycling of the medium 9 from 14, which participates according to the invention, in 20, in heat exchange with the bottom run-off 10 from 15, 10 then being fed into the upper part of column 14, if necessary after additional temperature correction; vapours 11, taken off at the top of 15, of the undesired accompanying substance from the mixture which forms an azeotrope (for example steam in the case of the ethanol/water mixture); and reflux 12 and take-off 13 of the condensed undesired accompanying substance.

EXAMPLE (Preparation of absolute ethanol from aqueous ethanol)

A plant for 60,000 tons per annum of absolute ethanol consists of 2 columns:

(a) an extractive distillation column with a diameter of 1.6 m and with 100 bubble cap trays (corresponding to 14 in the FIGURE) and (b) a regeneration column (corresponding to 15 in the FIGURE) with a diameter of 1.0 m and with 20 bubble cap trays.

The crude ethanol used as the feed product (7,900 kg/hour with 94% by weight of ethanol) is fed as a liquid at approximately boiling point (75° C.) and in a regulated quantity to the 35th tray of the extractive distillation column. At the top of this column, the absolute alcohol (with less than 200 ppm of water) is condensed at a pressure of 1,000 mbars in an air condenser, and is divided according to the reflux ratio R/T of 0.9. With the aid of the reflux, the vapours are stripped on the 96th to 100th trays, in order to keep the content of residual solvent below 1 ppm. Ethylene glycol is fed in at the 95th tray as the extraction solvent (14,300 kg/hour with less than 200 ppm of water) at a temperature of 85° C. and in a regulated quantity. The charge of ethanol is about 32% by weight. On the way downwards through the column, the ethanol in the ethylene glycol medium is replaced by water. Part of the ethylene glycol charged with about 2.7% by weight of water is pumped, at the bottom of the column, through the bottom heater, and the other part leaves the extractive distillation column with a temperature of about 184° C. This ethylene glycol charged with water is brought into heat exchange, in a heat exchanger (corresponding to 21 in the FIGURE), with column liquid which is taken off at the 15th tray of the extractive distillation column, and, after the end of the heat exchange process, is fed in, at a temperature of approximately 110° C., at the 10th tray of the regeneration column. The regeneration column is operated at a top pressure of 130 mbars. The water separated off in this column is condensed in an air condenser at 52° C. at the top of this 20-tray column, and, at a reflux ratio of R/T of 1, one half is taken off and the other half is recycled into the regeneration column for stripping with the vapours. The glycol which has been freed from water is partly pumped at the bottom of the regeneration column through a heating device, and is partly taken off at about 154° C. This stream of largely water-free ethylene glycol (less than 200 ppm of water) is brought into heat exchange, in a further heat exchanger, with a side-stream taken off at the 20th tray of the extractive distillation column, whereby the largely water-free ethylene glycol is cooled to a temperature of below 110° C. The residual cooling is effected in a down-stream water-cooled condenser (22). About 85% of the energy which is required to heat the media of the columns is recovered.

What is claimed is:

1. A process for the separation of components from a mixture which forms an azeotrope which comprises:
   (A) subjecting said mixture to an extractive distillation in an extractive distillation column by adding an extracting agent to said column and distilling over one of said components to leave behind another component and said extracting agent;
   (B) withdrawing said other component and said extracting agent as bottom, introducing the same into a regeneration column, distilling over said other component and withdrawing a bottoms comprising a major amount of said extracting agent;
   (C) withdrawing a first side stream from said extractive distillation column at a point between the bottom of the column and the feed point of said mixture, passing the same in heat exchange with the bottoms from said distillation column and returning the so-heat exchanged first side stream to said extractive distillation column at a point below the point at which it was withdrawn; and
   (D) withdrawing a second side stream from said extractive distillation column at a point between the bottom of the column and the feed point of said mixture, passing the same in heat exchange with the bottoms of said regeneration zone and returning the so-heat exchanged second side stream to said extractive distillation column at a point below the point at which it was withdrawn.

2. A process according to claim 1, wherein the first side stream is heat exchanged with the bottoms from said distillation column in a heat exchanger different from the heat exchanger employed to heat exchange said second side stream with the bottoms of said regeneration zone.

3. A process according to claim 2, wherein the bottoms of the regeneration zone are recycled to the extractive distillation column and fed therein as extracting agent.

4. A process according to claim 1, wherein the mixture to be separated contains one of the components in a quantity of from 0.1 to 30% by weight in addition to its proportion in the azeotrope.

5. A process according to claim 3, wherein the first side stream and second side stream are taken off from the extractive distillation column at different points.

6. A process according to claim 5, wherein the side stream taken off above is brought into heat exchange with the bottoms of the regeneration column and the side stream taken therebelow is brought into heat exchange with the bottoms of the extractive distillation column.

7. A process according to claim 1, wherein said mixture comprises a mixture of water and ethanol.

8. A process according to claim 1, wherein the extracting agent is ethylene glycol.

9. A process according to claim 7, wherein the extracting agent is ethylene glycol.

10. An apparatus for the extractive distillation of a mixture which form an azeotrope which comprises an extractive distillation column, a regeneration column, means for feeding an extracting agent into a said extractive distillation column, means for removing bottoms from said extractive distillation column and feeding the same into said regeneration column, means for withdrawing a first side stream from said extractive distillation column and passing the same in heat exchange from bottoms from said extractive distillation column and returning the so-heat exchanged first side stream to said extractive distillation column at a point below the point at which it is withdrawn, means for withdrawing a bottoms from said regeneration column, means for withdrawing a second side stream from said extractive distillation column, passing the same in heat exchange with the bottoms of said regeneration zone and returning the so-heat exchange second side stream to said extractive distillation column.

11. An apparatus according to claim 10, wherein there are two heat exchangers, one employed for heat exchange of said first side stream with the bottoms from distillation column and one employed for heat exchange of said second side stream with the bottoms of said regeneration zone.

12. An apparatus according to claim 10, wherein said distillation column comprises trays and there are 5 to 25 trays between the point at which the mixture to be separated is fed into the extractive distillation column and a point at which a side stream is withdrawn.

13. An apparatus according to claim 10, wherein said side streams are taken off at different points along the height of said extractive distillation column.

14. An apparatus according to claim 13, wherein said extractive distillation column comprises trays and there are 1 to 10 trays between the points at which the respective side streams are withdrawn.

* * * * *